United States Patent [19]
Houston

[11] Patent Number: 5,032,360
[45] Date of Patent: Jul. 16, 1991

[54] ODOR REMOVER

[76] Inventor: Reagan Houston, 252 Foxhunt La., Hendersonville, N.C. 28739

[21] Appl. No.: 259,461

[22] Filed: Oct. 14, 1988

Related U.S. Application Data

[63] Continuation-in-part of Ser. No. 61,448, Jun. 15, 1987, abandoned.

[51] Int. Cl.⁵ .............................................. A61L 9/03
[52] U.S. Cl. .................................... 422/4; 239/60; 422/5; 422/122; 422/123; 422/125; 422/126; 423/230; 423/245.1; 423/245.3
[58] Field of Search .................. 422/4, 5, 120, 122, 422/123, 125, 126, 300; 423/215.5, 230, 245 R, 245 S; 239/60

[56] References Cited

U.S. PATENT DOCUMENTS 2,254,906  9/1941  Petrulis ............................. 422/125
4,244,710  1/1981  Burger .................................. 422/5
4,600,557  7/1986  Spitz ..................................... 422/5

Primary Examiner—Robert J. Warden
Assistant Examiner—Timothy M. McMahon
Attorney, Agent, or Firm—David M. Carter

[57] ABSTRACT

There is provided an apparatus and method for removing odors from the air. The apparatus has a base with a candle mounted thereon and a container open at two ends located above the candle. The container houses activated charcoal. The candle causes the odor filled air to move through the container and thus through the activated charcoal by the chimney effect. Odors are removed from the air by the combustion of the candle, and by the activated charcoal and odors may also be masked by the scent of the candle.

5 Claims, 1 Drawing Sheet

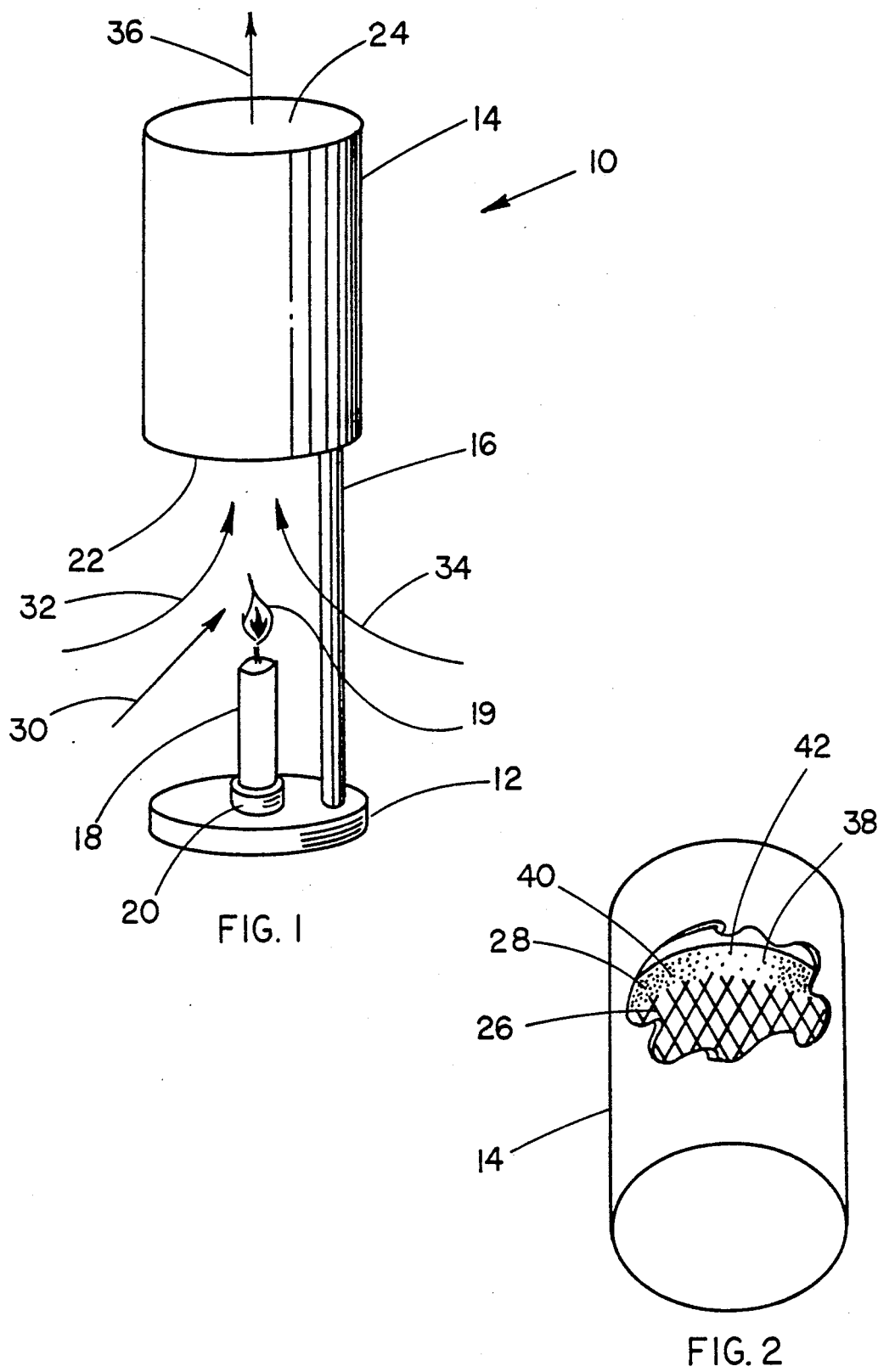

ODOR REMOVER

This is a continuation-in-part of co-pending appication Ser. No. 061,448 filed on June 15, 1987 now abandoned.

BACKGROUND OF THE INVENTION

This invention relates to devices for removing odors from the air. More particularly it relates to devices which are especially adapted to remove odor from air in the bathroom.

A problem which has long plagued mankind is how to remove odors from air inside one's house. Odors which remain in one's bathroom are particularly obnoxious. Commonly one strikes a match or lights a candle in the bathroom in an attempt to get rid of the odor. However, often this procedure results in merely masking the odors rather than removing them. Various attempts have been made in the past to provide devices for removing odor from the bathroom. One such device is disclosed in U.S. Pat. No. 1,774,156 issued to Root. The Root patent shows a device which draws odor directly from the toilet through granulated charcoal. However the Root design requires an electric fan and is rather complex. Other devices for removing odors are disclosed in U.S. Pat. Nos. RE 19,791, 4,244,710, 4,377,400 and 1,819,498. Furthermore, the use of adsorbent filters for removing odors is disclosed in the First Edition of R. H. Warring's *Filters and Filtration Handbook* on page 130. However it is believed that none of the above devices have met with commercial success when used in connection with removing odors in a bathroom.

OBJECTS OF THE INVENTION

It is therefore one object of this invention to provide an improved odor remover.

It is another object to provide a simple to construct and easy to operate device for removing odors from the air.

It is still another object to provide an odor remover which is inexpensive to manufacture and is easy to operate.

It is another object to provide an odor removal device which is particularly useful in the bathroom.

SUMMARY OF THE INVENTION

In accordance with one form of this invention there is provided an apparatus for removing odors from the air including a heat source. The apparatus further includes adsorption materials elevated from the heat source. The odors from the air are forced through the adsorption means by the upward movement of the heated air.

In accordance with another form of this invention, there is provided a method for removing odors from the air by heating the odor laden air with a combustion source and passing the heated air through an odor adsorption material. Preferably the heat source or combustion source is a candle and the adsorption material is activated charcoal, which is housed in a container with two open ends and located above the candle. The combustion products from the flame of the candle will help eliminate odors. Furthermore, in that the candle is located below the open ended container a chimney effect will occur causing the odor laden air to pass through the activated charcoal so that the odor may be adsorbed by the charcoal. The candle is located close enough to the activated charcoal so that at least a portion of the charcoal is heated to a temperature of 40° C. or greater. Also, by using a candle various candle fragrances may be utilized to further mask odors. Thus the subject apparatus may remove odor by at least two or preferably three mediums. Furthermore the candle will perform dual functions of both removing odor and causing the chimney effect to move odor laden air to contact the charcoal. Since various odors are most efficiently removed by different means, this combination is better than any of the three methods used separately.

BRIEF DESCRIPTION OF THE DRAWINGS

FIG. 1 is a perspective view showing the odor remover of the subject invention.

FIG. 2 is a partial perspective view of the container portion of the odor remover of FIG. 1 with part of the container being cut away.

DESCRIPTION OF THE PREFERRED EMBODIMENT

Referring now more particularly to FIG. 1, there is provided odor remover device 10 having base 12 and container 14 which are connected together by support beam 16. Because combustion is utilized with the odor remover, preferably the base, container and support beam are all made of metal. Preferably base 12 is at least twice as heavy as the container and support beam so that the odor remover will be stable. Candle 18 is mounted on base 12 and is held in place by candle holder 20 which is attached to base 12. Container 14 is preferably cylindrically shaped and is opened at ends 22 and 24 so that warm gases generated by candle 18 may pass through the container by the chimney effect.

Referring now to FIG. 2, circular wire mesh screen 26 is mounted inside of container 14 and is completely across one section of the container at approximately mid-level. The wire mesh screen provides support for a layer of activated charcoal 28 located above the screen. The activated charcoal is in the shape of a solid disk. Screen 26 is fine enough to hold the charcoal in place but coarse enough to permit odor laden air to readily pass therethrough. Preferably the layer of activated charcoal is approximately one inch thick permitting the odors from the air passing therethrough to be adsorbed thereon and oxidized thereby.

The odor remover device operates as follows: The device is placed in a room which is susceptible to unpleasant odors such as, for example, a bathroom. When odors occur in the bathroom, candle 18 is lit forming flame 19. Because the combustion of the candle requires oxygen, air will be drawn to the flame as indicated by arrow 30. That portion of the odor laden air indicated by arrow 30 will be treated by the combustion products of the candle, furthermore some of the odor will simply be oxidized by the flame of the candle. Preferably candle 18 is impregnated with pleasant scents such as pine scents which upon burning will give off a pleasant odor, thus masking some of the unpleasant odors in the bathroom. Since the heat generated by the flame of the candle will travel upwardly, odor laden air indicated by arrows 32 and 34 will travel up into the bottom opening 22 of container 14 and the heated air with most of the odor removed, will pass through the top 24 of the container as indicated by arrow 36. The passing of the air through the container is accomplished due to the chimney effect.

The odors in the air passing through container 14 will be adsorbed onto activated charcoal 28. Preferably the charcoal is activated with potassium carbonate. The outer portions of 38 and 40 of the activated charcoal will adsorb the odor better than the central portion 42 because the central portion 22 will be at a higher temperature due to the flame 19.

Although outer portions of the activate charcoal will adsorb more odors, the inner portion, being hotter, will more quickly oxidize the odors. Furthermore, with time some of the odors in the cooler portions will desorb and become adsorbed on the warmer portions for oxidization thereof. Thus adsorption and oxidation of odors will occur simultaneously and continuously while the device is operating. The position of the candle flame with respect to the charcoal 28 is such that the temperature of at least a portion of the charcoal will rise to at least 40° C. Preferably the temperature of the inner or central portion of the charcoal which is directly below the flame will rise to at least 50° C. It is also preferred that the temperature difference between the hotter inner portion of the charcoal and the cooler outer portion be at least 10° C. so that adsorption and oxidation in the charcoal will take place efficiently.

Thus the candle used with activated charcoal situated above it presents multiple functions, namely the candle eliminates certain odors and also provides a chimney effect to cause other odor laden air to move through the activated charcoal. Furthermore by using both a candle and activated charcoal, certain odors which are more easily destroyed by the candle flame will be removed while other odors which are more easily adsorbed and oxidized by the activated charcoal will also be removed thus a broader spectrum of odors may be removed from the air than with prior devices. Also because a candle is the heat source, the candle may be impregnated with a pleasant odor to mask odors which might escape the candle flame and the activated charcoal.

From the above description of the preferred embodiment, it will be apparent that many modifications may be made therein without departing from the true spirit and scope of this invention. It is therefore intended in the accompanying claims to cover all such modifications.

I claim:

1. A method for removing odors from odor ladened air comprising the steps of:
   heating the odor ladened air with the flame of a candle; said candle being made of a scent containing wax;
   combusting portions of said odor in said odor ladened air with said flame;
   positioning said candle below an absorptive material; said absorptive material being activated charcoal;
   passing said heated odor ladened air through said charcoal by the chimney effect;
   heating first portions of said charcoal to at least 40° C.; other portions of said charcoal being at least 10° cooler than said first portions;
   absorbing portions of said odors in said odor ladened air onto said charcoal oxidizing said odors in said first portions of said charcoal; dynamically desorbing unoxidized odors from said other portions of said charcoal, and adsorbing said desorbed odors on said first portions of said charcoal; oxidizing said desorbed odors on said first portions of said charcoal.

2. A method as set forth in claim 1 wherein said charcoal includes a central region and an outer region and further including the step of heating the central region of said charcoal to a temperature higher than the outer region whereby more absorption will take place in said outer region than in said central region and oxidation will proceed faster in said central region than in said outer region.

3. A method as set forth in claim 1 further including the step of emitting scented material into the air.

4. A method as set forth in claim 1 further including the steps of emitting products of combustion from said flame and masking said odors with said products of combustion.

5. A method for removing odors from air comprising the steps of:
   oxidizing portions of said odors in a flame of a candle;
   heating said air by said flame;
   positioning said candle below an absorbent bed;
   conducting said heat upwardly by the chimney effect through said absorbent bed;
   heating portions of said bed to a temperature higher than other portions; said higher temperature being at least 40° C.; said absorbent bed being shaped to permit temperature differentials of at least 10° C. in different portions thereof;
   adsorbing most of said odors in said heated air on the cooler portion of said bed;
   rapidly oxidizing said odors in the hotter portion of said bed;
   dynamically desorbing unoxidized odors from said cooler portion to said hotter portion of said bed; adsorbing said desorbed odors on said hotter portion of said bed; oxidizing said desorbed odors in said hotter portion of said bed.
   heating said air by said flame;
   conducting said heated air upwardly by the chimney effect through an absorbent bed;
   heating portions of said bed to a temperature at least 10° higher than other portions of said bed;
   adsorbing third portions of said odors in said heated air on the cooler portion of said bed;
   rapidly oxidizing said odors in the hotter portion of said bed, thereby removing fourth portions of said odors; dynamically desorbing unoxidized odors from said cooler portion to said hotter portion of said bed, oxidizing said desorbed odors in said hotter portion of said bed thereby removing said third portion of said odors.

* * * * *